United States Patent
De Simone

(10) Patent No.: US 6,380,252 B1
(45) Date of Patent: Apr. 30, 2002

(54) USE OF L-ACETYLCARNITINE, L-ISOVALERYLCARNITINE, L-PROPIONYLCARNITINE FOR INCREASING THE LEVELS OF IGF-1

(75) Inventor: Claudio De Simone, Ardrea (IT)

(73) Assignees: Sigma-Tau Industrie Farmaceutiche Riunite S.p.A., Rome; Mendes S.R.L., Ardea, both of (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/510,669

(22) Filed: Feb. 22, 2000

Related U.S. Application Data

(63) Continuation-in-part of application No. 09/510,672, filed on Feb. 22, 2000, now Pat. No. 6,166,077, which is a continuation of application No. 09/147,465, filed as application No. PCT/IT97/00113 on May 15, 1997, now Pat. No. 6,037,373.

(51) Int. Cl.$^7$ .............................................. A61K 31/205
(52) U.S. Cl. ....................... 514/556; 424/400; 424/489; 514/228.8
(58) Field of Search ................................ 514/556, 228.8

(56) References Cited

U.S. PATENT DOCUMENTS 6,166,077 A * 12/2000 De Simone ................. 514/556

* cited by examiner

Primary Examiner—Thurman K. Page
Assistant Examiner—Charesse L. Evans
(74) Attorney, Agent, or Firm—Oblon, Spivak, McClelland, Maier & Neustadt, P.C.

(57) ABSTRACT

A method is provided for increasing the levels of IGF-1 for the therapeutic treatment or prophylaxis of cytological disorders or diseases related to IGF-1 selected from the group including neuropathies of the optic nerve and of the olfactory nerve, neuralgia of the trigmeninal nerve, Bell's paralysis, amyotrophic lateral sclerosis, osteoporosis, anthropathy, arthritis, cervical spondylosis and hernia of the intervertebral discs clinical syndromes of reduced height, cachexia and acute or chronic hepatic necrosis, Turner's syndrome, sarcopoenia, growth hormone insensitivity syndromes, obesity, asthenia, myasthenia and heart asthenia, immunodeficiencies and reperfusion injuries, and for the cicatrization of wounds, the healing of ulcers, the treatment of burns, tissue regeneration, cutaneous, intestinal and hepatic tissue regeneration and the formation of dentine, that includes administering, to a patient in need thereof, at least one selected from the group including L-acetylcarnitine, L-isovalerylcarnitine, and L-propionylcarnitine or pharmacologically acceptable salts thereof. The present invention also relates to a method and composition for treating HCV and/or increasing the levels of IGF-1 of a patient in need thereof, the composition including at least one selected from the group including L-acetylcarnitine, L-isovalerylcarnitine, L-propionylcarnitine and pharmacologically acceptable salts thereof and mixtures thereof; and at least one selected from the group including L-carnitine, coenzyme Q10, vitamin E and Se-L-methionine and pharmaceutically acceptable salts and derivatives thereof and mixtures thereof.

20 Claims, No Drawings

USE OF L-ACETYLCARNITINE, L-ISOVALERYLCARNITINE, L-PROPIONYLCARNITINE FOR INCREASING THE LEVELS OF IGF-1

This application is a continuation-in-part of U.S. patent application Ser. No. 09/510,672, filed Feb. 22, 2000, now U.S. Pat. No. 6,166,077, which is a continuation of U.S. patent application Ser. No. 09/147,465, filed as national stage application no. PCT/IT97/00113 on May 15, 1997, now U.S. Pat. No. 6,037,373.

BACKGROUND OF THE INVENTION

Field of the Invention

The present invention relates to a novel therapeutic use of L-acetylcarnitine, L-isovalerylcarnitine, L-propionylcarnitine or pharmacologically acceptable salts thereof for increasing the levels of IGF-1 (insulin-like growth factor 1) for the therapeutic treatment or prophylaxis of cytological disorders or diseases related to IGF-1. More particularly, the present invention relates to the use of L-acetylcarnitine, L-isovalerylcarnitine, L-propionylcarnitine or pharmacologically acceptable salts thereof for the therapeutic treatment or prophylaxis of individuals in whom IGF-1 contributes towards the pathogenesis of a particular disease or provokes cytological disorders. The present invention also relates to the use of any of L-acetylcarnitine, L-isovalerylcarnitine, L-propionylcarnitine or pharmacologically acceptable salts thereof in combination with any of L-carnitine, coenzyme Q10, vitamin E and/or Se-L-methionine and pharmaceutically acceptable salts and derivatives thereof in the treatment of hepatitis-C virus and/or for increasing the levels of IGF-1.

Like other growth factors, IGF-1 promotes cell growth and differentiation. The administration of IGF-1 obtained as a protein purified by molecular biology methods has made it possible to confirm the effects observed in vitro with cells, on animal models and in man. Essentially, the action of IGF-1 is similar to that of insulin, that is to say an increase in the uptake of glucose, a reduction in ketones and fatty acids in the serum and an increase in protein synthesis. In accordance with these and other metabolic effects, clinical studies have been undertaken in order to evaluate the efficacy of IGF-1 in a range of diseases. IGF-1 has been administered to patients with type-II diabetes, to cachectic patients, to patients with ischemic damage at the neuronal, myocardial or renal level, and has been proposed for repairing and regenerating tissues (W. L. Lowe, Insulin-like growth factors, Scientific American Science and Medicine p. 62, March 1996).

From the above, it is clear that the administration of IGF-1 may be therapeutically useful in various morbid conditions. Examples of diseases or disorders which may be prevented, cured or improved by the administration of IGF-1 include neuropathies of the optic nerve and of the olfactory nerve, neuralgia of the trigeminal nerve, Bell's paralysis, amyotrophic lateral sclerosis and other motor neuron diseases, degeneration of the retina, osteoporosis, arthropathy, arthritis, cervical spondylosis and hernia of the intervertebral discs, clinical syndromes of reduced height, cachexia, acute or chronic hepatic necrosis, Turner's syndrome, sarcopoenia, growth hormone insensitivity syndromes, diabetes, obesity, asthenia in general and in particular myasthenia and heart asthenia, immunodeficiencies and reperfusion injuries. IGF-1 moreover appears to be useful for the cicatrization of wounds, the healing of ulcers, the treatment of burns, tissue regeneration in general and in particular that of cutaneous, intestinal and hepatic tissue, and the formation of dentine.

Unfortunately, the administration of IGF-1 in man brings about undesirable effects such as oedema, pain in the temporomandibular joint and arthralgia. These symptoms are such as to prevent the administration of IGF-1 from being recommended or are responsible for interrupting the treatment. It is therefore necessary to find novel substances which are capable of inducing the production of IGF-1.

In addition, hepatitis C virus (HCV) is the most common cause of viral hepatitis in the developed world. In some populations of the Middle East the incidence of antibodies against HCV peaks up to 6%. Despite many advances in the knowledge of HCV, the pathogenesis of this infection is still not characterized in all its aspects. In particular, it is not presently known how HCV causes hepatic cell injury; the histological findings of the livers of HCV-infected patients revealing a variety of complex interactions between host and viral factors. The most striking observation at the ultrastructural level is the severe alteration in the mitochondria of hepatocytes from patients who are HCV-infected. The dysfunction of the mitochondria leads to the promotion of both immune- and non-immune-mediated death of the hepatocyte. In chronic HCV infection, this sequence of events leads to chronic hepatic necrosis and finally even to cirrhosis in advanced disease.

Even though the "standard" treatment of HCV-infected patients is based on the use of interferons—mainly alpha-IFN (α-IFN), eventually in association with other antivirals (i.e. ribavirin), the inventors surprisingly found that compositions that contain any of L-acetylcarnitine, L-isovalerylcarnitine, L-propionylcarnitine or pharmacologically acceptable salts thereof in combination with any of L-carnitine, coenzyme Q10, Vitamin E and/or Se-L-Methionine and pharmaceutically acceptable salts and derivatives thereof can lead to new therapeutic strategies for HCV treatment as well as other conditions where IGF-1 levels are deficient and which lead to increased and/or prolonged cell death (i.e. HIV-infection, retinal damage, and also those noted above). This formulation can be given as dietary supplement or as a drug.

According to one embodiment of the present invention, the administration of L-acetylcarnitine, L-isovalerylcarnitine, L-propionylcarnitine or pharmacologically acceptable salts thereof is capable of inducing the production of IGF-1 without the undesirable effects produced by the administration of exogenous IGF-1.

According to another embodiment of the present invention, the administration of any of L-acetylcarnitine, L-isovalerylcarnitine, L-propionylcarnitine or pharmacologically acceptable salts thereof in combination with any of L-carnitine, coenzyme Q10, vitamin E and/or Se-L-methionine and pharmaceutically acceptable salts and derivatives thereof can lead to new therapeutic strategies for HCV treatment as well as other conditions where IGF-1 levels are deficient.

In the description which follows, the expression pharmacologically acceptable salt of L-acetylcarnitine, of L-isovalerylcarnitine or of L-propionylcarnitine is understood to refer to any salt of the above with an acid which does not give rise to undesirable toxicity or side-effects. Such acids are well known to pharmacologists and to experts in the pharmaceutical field.

Non-limiting examples of such salts are; chloride; bromide; iodide; aspartate, in particular hydrogen aspartate;

citrate, in particular hydrogen citrate; tartrate; phosphate, in particular hydrogen phosphate; fumarate, in particular hydrogen fumarate; glycerophosphate, glucose phosphate; lactate; maleate, in particular hydrogen maleate; orotate; oxalate, in particular hydrogen oxalate; sulphate, in particular hydrogen sulphate; trichloroacetate, trifluoroacetate and methanesulphonate.

In the description which follows, for the purposes of brevity and for ease of explanation, reference will be made only to L-acetylcarnitine, it being understood that the description given applies also to the above-mentioned L-isovalerylcarnitine and L-propionylcarnitine and to pharmacologically acceptable salts thereof.

Therapeutic uses of L-acetylcarnitine, L-isovalerylcarnitine and L-propionylcarnitine for the therapeutic treatment of myocardial arrhythmia and ischemia, peripheral functional vasculopathy of the arteries, senile dementia, peripheral neuropathies and myopathies are already previously known. For instance, EP 0 516 594 A1, the entire contents of which are hereby incorporated by reference, discloses the use of propionyl- and isovaleryl L-carnitine for treating myopathies, neuronal degeneration and for inhibiting proteolysis. Cardiov. Res. 1986, 20:536–541, the entire contents of which are hereby incorporated by reference, deals with the protection of the ischaemic myocardium by propionyl L-carnitine. Docum. Ophtal. 1988, 70:89–96, the entire contents of which are hereby incorporated by reference, hints at therapeutic potentialities of acetyl L-carnitine in diabetes and diabetic complications of the visual system. However, there is no correlation between these known therapeutic uses and the subject of the present invention.

It has now been found, surprisingly, that L-acetylcarnitine, L-isovalerylcarnitine, L-propionylcarnitine or pharmaceutically acceptable salts thereof are capable of increasing the levels of IGF-1 in human biological fluids. It should be emphasized that, on the basis of extensive supporting scientific literature, the mechanism of action of L-acetylcarnitine has been focused at the metabolic level, more specifically demonstrating a protective action with respect to the mitochondria, whereas the present invention demonstrates an action mediated by the production of IGF-1.

In one embodiment of the present invention, the L-acetylcarnitine, L-isovalerylcarnitine, L-propionylcarnitine or pharmaceutically acceptable salts thereof are administered in combination with vasodilatory, vascular, endocrinological, immunological, cytostatic, immunomodulatory, anti-inflammatory or cortisone pharmaceutical products, IGF-1, IGF-1 binding proteins, growth hormones and other cell growth factors such as, for example, epidermal growth factor, and erythropoietin.

According to another embodiment of the present invention, the administration of any of L-acetylcarnitine, L-isovalerylcarnitine, L-propionylcarnitine or pharmacologically acceptable salts thereof in combination with any of L-carnitine, coenzyme Q10, vitamin E and/or Se-L-methionine and pharmaceutically acceptable salts and derivatives thereof can lead to new therapeutic strategies for HCV treatment as well as other conditions where IGF-1 levels are deficient.

Various preferred embodiments of the invention, A–M, which are not intended to be limiting, are listed below.

A. A method for increasing the levels of IGF-1 for the therapeutic treatment or prophylaxis of cytological disorders or diseases related to IGF-1 selected from the group consisting of neuropathies of the optic nerve and of the olfactory nerve, neuralgia of the trigeminal nerve, Bell's paralysis, amyotrophic lateral sclerosis and other motor neuron diseases, degeneration of the retina, osteoporosis, arthropathy, arthritis, cervical spondylosis and hernia of the intervertebral discs, clinical syndromes of reduced height, cachexia and acute or chronic hepatic necrosis, Turner's syndrome, sarcopoenia, growth hormone insensitivity syndromes, diabetes, obesity, asthenia in general and in particular myasthenia and heart asthenia, immunodeficiencies and reperfusion injuries, and for the cicatrization of wounds, the healing of ulcers, the treatment of burns, tissue regeneration in general and in particular that of cutaneous, intestinal and hepatic tissue, and the formation of dentine, that includes:

administering, to a patient in need thereof, at least one selected from the group consisting of L-acetylcarnitine, L-isovalerylcarnitine, and L-propionylcarnitine or pharmacologically acceptable salts thereof.

B. The method of A, in which the L-acetylcarnitine, L-isovalerylcarnitine, I-propionylcarnitine or pharmacologically acceptable salts thereof are administered in combination with at least one selected from the group consisting of vasodilatory, vascular, endocrinological, immunological, cytostatic, immunomodulatory, anti-inflammatory or cortisone pharmaceutical products, IGF-1, IGF-1 binding proteins, growth hormones and epidermal growth factor, and erythropoietin.

C. The method of A, in which L-acetylcarnitine is administered.

D. The method of A, in which L-isovalerylcarnitine is administered.

E. The method of A, in which L-propionylcarnitine is administered.

F. The method of A, wherein 0.01 mg–15 g per day of L-acetylcarnitine are administered.

G. The method of A, wherein 0.1 mg–10 g per day of L-acetylcarnitine are administered.

H. The method of A, wherein 0.01 mg–15 g per day of L-isovalerylcarnitine are administered.

I. The method of A, wherein 0.1 mg–10 g per day of L-isovalerylcarnitine are administered.

J. The method of A, wherein 0.01 mg–10 g per day of L-propionylcarnitine are administered.

K. The method of A, wherein 0.1 mg–10 g per day of L-propionylcarnitine are administered.

L. A pharmaceutical composition which may be administered orally, parenterally, nasally or topically for increasing the levels of IGF-1 for the therapeutic treatment or prophylaxis of cytological disorders or diseases related to IGF-1, selected from the group comprising neuropathies of the optic nerve and of the olfactory nerve, neuralgia of the trigeminal nerve, Bell's paralysis, amyotrophic lateral sclerosis and other motor neuron diseases, degeneration of the retina, osteoporosis, arthropathy, arthritis, cervical spondylosis and hernia of the intervertebral discs, clinical syndromes of reduced height, cachexia and acute or chronic hepatic necrosis, Turner's syndrome, sarcopoenia, growth hormone insensitivity syndromes, diabetes, obesity, asthenia, myasthenia and heart asthenia, immunodefidences and reperfusion injuries, and for the cicatrization of wounds, the healing of ulcers, the treatment of burns, tissue regeneration particularly that of cutaneous, intestinal and hepatic tissue, and the formation of dentine, the composition including, as active principle, an amount of L-acetylcarnitine, L-isovalerylcarnitine, L-propionylcarnitine or of pharmacologically acceptable salts thereof which is effective for increasing the levels of IGF-1, and at least one pharmacologically acceptable excipient.

M. A method for increasing the levels of IGF-1 for the therapeutic treatment or prophylaxis of cytological disorders or diseases related to IGF-1 selected from the group including neuropathies of the optic nerve and of the olfactory nerve, neuralgia of the trigmeninal nerve, Bell's paralysis, amyotrophic lateral sclerosis, osteoporosis, anthropathy, arthritis, cervical spondylosis and hernia of the intervertebral discs clinical syndromes of reduced height, cachexia and acute or chronic hepatic necrosis, Turner's syndrome, sarcopenia, growth hormone insensitivity syndromes, obesity, asthenia, myasthenia and heart asthenia, immunodeficiences and reperfusion injuries, and for the cicatrization of wounds, the healing of ulcers, the treatment of burns, tissue regeneration, cutaneous, intestinal and hepatic tissue regeneration and the formation of dentine, that includes orally, parenterally, nasally or topically administering, to a patient in need thereof, a composition, that includes, as active ingredients at least one selected from the group including L-acetylcarnitine, L-isovalerylcarnitine, L-propionylcarnitine and pharmacologically acceptable salts thereof and mixtures thereof; and at least one selected from the group including L-carnitine, coenzyme Q10, vitamin E and Se-L-methionine and pharmaceutically acceptable salts and derivatives thereof and mixtures thereof.

EXAMPLES

The examples which follow are for the purpose of illustrating the invention and should in no way be understood as implying a limitation in the scope thereof.

Example 1

13 individuals infected with HIV were enrolled. Blood was taken before and after treatment with L-acetylcarnitine orally at a dosage of 3 g/day for 8 weeks. The levels of IGF-1 were measured using a kit supplied by Amersham Itaha s.r.l., Milan, and the results were expressed as ng of IGF-1/100 µl of serum.

TABLE 1

| Patient # | Before | After |
|---|---|---|
| 1 | 0.03 | 4.16 |
| 2 | 0.03 | 5 |
| 3 | 0.03 | 0.06 |
| 4 | 0.02 | 5 |
| 5 | 0.02 | 0.05 |
| 6 | 0.04 | 3.25 |
| 7 | 0.25 | 5 |
| 8 | 0.02 | 0.03 |
| 9 | 0.1 | 5 |
| 10 | 0.07 | 5 |
| 11 | 0.03 | 5 |
| 12 | 0.16 | 3.49 |
| 13 | 0.03 | 0.18 |
| AVERAGE | 0.06 | 3.17 |
| Standard deviation | 0.07 | 2.22 |
| Standard error | 0.02 | 0.62 |
| Student test | | 0.0002 |

It is known that individuals infected with HIV can have variable levels of IGF-1 in their serum. The experiments reported here demonstrated that the oral administration of L-acetylcarnitine increases the levels of IGF-1 in peripheral blood.

Example 2

Four Patients aged above 70 and with healthy dispositions were treated with 2 grams/day of L-acetylcarnitine parenterally for 7 days. The results of the doses of IGF-1 before and after the treatment are reported in Table 2.

TABLE 2

| Patient # | Before | After |
|---|---|---|
| 1 | 0.01 | 2.1 |
| 2 | 0.02 | 3.6 |
| 3 | 0.05 | 1.8 |
| 4 | 0.03 | 3.8 |
| AVERAGE | 0.03 | 2.83 |
| Standard deviation | 0.02 | 1.02 |
| Standard error | 0.008 | 0.51 |
| Student test | | 0.01 |

Example 3

In this example, 60 subjects with chronic HCV infection were divided into three groups as follows:
A. to be treated with the formulation (2 sachets/day);
B. to be treated with the formulation plus α-IFN (18 millions/week); and
C. to be treated with α-IFN and the formulation at the above dosage; and were treated with a composition containing the following:

| ACTIVE INGREDIENTS (POTENCY 100%): | |
|---|---|
| L-Carnitine base | mg 100 |
| Acetyl-L-Carnitine HCl | mg 100 |
| Coenzyme Q10 | mg 20 |
| Vitamin E | mg 10 |
| Se-L-Methionine | mcg 50. |

Derivatives of the described active ingredients (corrected to potency 100%) may be also be used.

Inactive Components
D-Mannitol
Sucrose
Saccharin Sodium
Providone
Flavouring Agents
Colouring Agents
Purified Water (not present in the final product)
Ethanol (not present in the final product).

The length of the treatment was one month followed by another 4 weeks of follow-up. All the patients were examined before treatment, after one month and after two months for clinical signs and symptoms related to their illness, side effects or toxicities. In addition the efficacy (or inefficacy) of the composition was monitored by measuring liver enzymes—as parameters of hepatic necrosis-, IGF-1 levels and mitochondrial functionality, at the different time points.

The present invention can lead to a new therapeutic strategy for HCV treatment as well as other conditions where IGF-1 levels are deficient and lead to increased and/or prolonged cell death (i.e. HIV-infection, retinal damage, etc . . . such as those listed above). This formulation can be given as dietary supplement or as a drug.

Other inactive components may be also used in addition to or in place of those listed above. Preferred examples thereof include acidifying agents (citric acid, fumaric acid, hydrochloric acid, malic acid etc.); alkalinizing agents (sodium bicarbonate, potassium citrate, sodium citrate, sodium carbonate etc.); cellulose (different types and grades); derivatives of cellulose (different types and grades); sorbitol; polyethylene glycols (different grades); colloidal silicon dioxide; magnesium stearate; stearic acid; starch (different types and grades); emulsifying agents; preservatives; chelating agents; glidants; diluents; granulating agents; and solvents.

The entire contents of each of U.S. application Ser. No. 09/147,465, filed Jan. 4, 1999; international application PCT/IT97/00113, filed May 15, 1997; and Italian application RM 96 A 000479, filed Jul. 5, 1996 are hereby incorporated by reference.

What is claimed is:

1. A method for increasing the level of IGF-1, comprising administering to a patient in need thereof a composition, comprising, as active ingredients:
   at least one selected from the group consisting of L-acetylcarnitine, L-isovalerylcarnitine, L-propionylcarnitine and pharmacologically acceptable salts thereof and mixtures thereof; and
   at least one selected from the group consisting of L-carnitine, coenzyme Q10, vitamin E and Se-L-methionine and pharmaceutically acceptable salts and derivatives thereof and mixtures thereof.

2. The method of claim 1, wherein said composition comprises L-carnitine or a pharmacologically acceptable salt thereof.

3. The method of claim 2, wherein said pharmacologically acceptable salt is a chloride, bromide, iodide, aspartate, hydrogen aspartate, citrate, hydrogen citrate, tartrate, phosphate, hydrogen phosphate, fumarate, hydrogen fumarate, glycerophosphate, glucose phosphate, lactate, maleate, hydrogen maleate, orotate, oxalate, hydrogen oxalate, sulfate, hydrogen sulfate, trichloroacetate, trifluoroacetate, or methanesulphonate.

4. The method of claim 1, wherein said composition comprises coenzyme Q10.

5. The method of claim 1, wherein said composition comprises vitamin E.

6. The method of claim 1, wherein said composition comprises Se-L-methionine or a pharmacologically acceptable salt thereof.

7. The method of claim 6, wherein said pharmacologically acceptable salt is a chloride, bromide, iodide, aspartate, hydrogen aspartate, citrate, hydrogen citrate, tartrate, phosphate, hydrogen phosphate, fumarate, hydrogen fumarate, glycerophosphate, glucose phosphate, lactate, maleate, hydrogen maleate, orotate, oxalate, hydrogen oxalate, sulfate, hydrogen sulfate, trichloroacetate, trifluoroacetate, or methanesulphonate.

8. The method of claim 1, wherein said composition comprises L-acetylcarnitine, L-isovalerylcarnitine, L-propionylcarnitine and/or pharmacologically acceptable salts thereof.

9. The method of claim 8, wherein said pharmacologically acceptable salt is a chloride, bromide, iodide, aspartate, hydrogen aspartate, citrate, hydrogen citrate, tartrate, phosphate, hydrogen phosphate, fumarate, hydrogen fumarate, glycerophosphate, glucose phosphate, lactate, maleate, hydrogen maleate, orotate, oxalate, hydrogen oxalate, sulfate, hydrogen sulfate, trichloroacetate, trifluoroacetate, or methanesulphonate.

10. The method of claim 1, wherein said composition comprises L-acetylcarnitine or a pharmacologically acceptable salt thereof.

11. The method of claim 10, wherein said pharmacologically acceptable salt is a chloride, bromide, iodide, aspartate, hydrogen aspartate, citrate, hydrogen citrate, tartrate, phosphate, hydrogen phosphate, fumarate, hydrogen fumarate, glycerophosphate, glucose phosphate, lactate, maleate, hydrogen maleate, orotate, oxalate, hydrogen oxalate, sulfate, hydrogen sulfate, trichloroacetate, trifluoroacetate, or methanesulphonate.

12. The method of claim 1, wherein said composition comprises L-isovalerylcarnitine or a pharmacologically acceptable salt thereof.

13. The method of claim 12, wherein said pharmacologically acceptable salt is a chloride, bromide, iodide, aspartate, hydrogen aspartate, citrate, hydrogen citrate, tartrate, phosphate, hydrogen phosphate, fumarate, hydrogen fumarate, glycerophosphate, glucose phosphate, lactate, maleate, hydrogen maleate, orotate, oxalate, hydrogen oxalate, sulfate, hydrogen sulfate, trichloroacetate, trifluoroacetate, or methanesulphonate.

14. The method of claim 1, wherein said composition comprises L-propionylcarnitine or a pharmacologically acceptable salt thereof.

15. The method of claim 14, wherein said pharmacologically acceptable salt is a chloride, bromide, iodide, aspartate, hydrogen aspartate, citrate, hydrogen citrate, tartrate, phosphate, hydrogen phosphate, fumarate, hydrogen fumarate, glycerophosphate, glucose phosphate, lactate, maleate, hydrogen maleate, orotate, oxalate, hydrogen oxalate, sulfate, hydrogen sulfate, trichloroacetate, trifluoroacetate, or methanesulphonate.

16. The method of claim 1, wherein said composition further comprises a pharmaceutically acceptable excipient.

17. The method of claim 1, wherein said composition is administered orally, parenterally, nasally, or topically.

18. The method of claim 1, wherein 0.01 mg to 15 g per day of active ingredients are administered.

19. The method of claim 1, wherein 0.1 mg to 10 g per day of active ingredients are administered.

20. The method of claim 1, wherein said pharmacologically acceptable salt is a chloride, bromide, iodide, aspartate, hydrogen aspartate, citrate, hydrogen citrate, tartrate, phosphate, hydrogen phosphate, fumarate, hydrogen fumarate, glycerophosphate, glucose phosphate, lactate, maleate, hydrogen maleate, orotate, oxalate, hydrogen oxalate, sulfate, hydrogen sulfate, trichloroacetate, trifluoroacetate, or methanesulphonate.

* * * * *

UNITED STATES PATENT AND TRADEMARK OFFICE
CERTIFICATE OF CORRECTION

PATENT NO.     : 6,380,252 B1
DATED          : April 30, 2002
INVENTOR(S)    : De Simone It is certified that error appears in the above-identified patent and that said Letters Patent is hereby corrected as shown below:

<u>Title page,</u>
Item [30], Foreign Application Priority Data, information should read:

-- [30]        Foreign Application Priority Data
       Jul. 5, 1996     (IT) ........................ RM96A0479

Signed and Sealed this

Fourteenth Day of January, 2003

JAMES E. ROGAN
*Director of the United States Patent and Trademark Office*